United States Patent [19]

Bowman

[11] 4,276,294
[45] Jun. 30, 1981

[54] BENZOFURYLPIPERAZINES

[75] Inventor: Robert M. Bowman, Summit, N.J.

[73] Assignee: Ciba-Geigy Corporation, Ardsley, N.Y.

[21] Appl. No.: 135,799

[22] Filed: Mar. 31, 1980

Related U.S. Application Data

[63] Continuation-in-part of Ser. No. 960,405, Nov. 30, 1978, abandoned.

[51] Int. Cl.$^3$ .................. A61K 31/495; C07D 405/04
[52] U.S. Cl. ............................... 424/250; 260/346.73; 424/282; 424/285; 544/376; 544/378; 544/388
[58] Field of Search ............... 544/376, 378; 424/250, 424/285, 282; 260/346.73

[56] References Cited

U.S. PATENT DOCUMENTS

| 3,374,245 | 3/1968 | Carney et al. | 544/376 |
| 3,773,759 | 11/1973 | Cusic et al. | 544/376 |
| 4,009,184 | 2/1977 | Kaupmann et al. | 260/346.73 |

OTHER PUBLICATIONS

Tseng et al., *J. Org. Chem.*, vol. 38, No. 9, pp. 1746–1747, (1973).

*Primary Examiner*—Paul M. Coughlan, Jr.
*Attorney, Agent, or Firm*—Prabodh I. Almaula

[57] ABSTRACT 1-(2-phenyl-3-benzofuryl)-piperazines, e.g. those of the formula

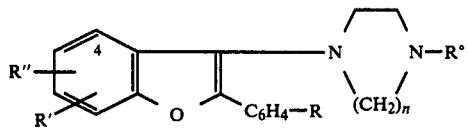

R=H, alkyl or halo
R', R''=H, alkyl, alkoxy, alkylenedioxy, alkylthio or halo
R°=H, alkyl or hydroxyalkyl
n=2 or 3 acyl derivatives, quaternaries and salts thereof are anticonvulsants.

8 Claims, No Drawings

BENZOFURYLPIPERAZINES

CROSS-REFERENCE TO RELATED APPLICATION

This is a continuation-in-part of application Ser. No. 960,405, filed Nov. 30, 1978 (now abandoned).

SUMMARY OF THE INVENTION

The present invention concerns and has for its object the provision of novel 1-(2-phenyl-3-benzofuryl)-piperazines, more particularly of those corresponding to Formula I

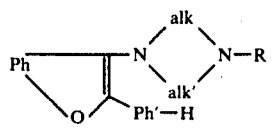

wherein each of Ph and Ph' is 1,2-phenylene, unsubstituted or substituted by up to 3 members selected from the group consisting of lower alkyl, hydroxy, lower alkoxy, benzyloxy, lower alkylenedioxy, lower alkylthio, halogeno, trifluoromethyl, nitro, amino, lower alkylamino and di-lower alkylamino; each of the radicals alk and alk' is lower alkylene separating both nitrogens by 2 or 3 carbon atoms and R is hydrogen, lower or higher alkyl or alkanoyl, lower alkoxycarbonyl, lower alkenyl, lower alkynyl or lower hydroxyalkyl, wherein the multiple bond or hydroxy group is separated from the nitrogen atom by at least 2 carbon atoms; of lower alkylquaternaries and pharmaceutically acceptable acid addition salts thereof; of corresponding pharmaceutical compositions and of methods for the preparation and application of these products, which are useful anticonvulsant agents, for example, in the treatment or management of epilepsy and other spastic conditions.

DESCRIPTION OF THE PREFERRED EMBODIMENTS

The 1,2-phenylene radical Ph and the ortho-unsubstituted phenyl radical H-Ph' contain preferably but one or two substituents, advantageously one in para-position relative to 1-oxy, and none in Ph'. Said substituents are, for example, methyl, ethyl, n- or i-(propyl or butyl) or t-butyl; hydroxy, methoxy, ethoxy, n- or i-(propoxy or butoxy); benzyloxy; methylenedioxy or ethylidenedioxy; methylthio or ethylthio; fluoro, chloro or bromo; trifluoromethyl; nitro; amino, mono- or dimethylamino.

At least one of the lower alkylene groups alk and alk' is preferably ethylene, but they may also represent 1,2- or 1,3-propylene; 1,2-, 1,3- or 2,3-butylene; thus forming with the nitrogen atoms preferably the piperazino or homopiperazino moiety.

The 4-substituent R thereof is preferably one of said lower alkyl groups, especially methyl; and also n- or i-(pentyl, hexyl or heptyl). A higher alkyl group is preferably n-(octyl, nonyl, decyl, undecyl, dodecyl, tetradecyl, hexadecyl or octadecyl). Corresponding alkanoyl or alkoxycarbonyl radicals are, for example, acetyl, propionyl, pivaloyl, valeryl, caproyl, decanoyl, lauroyl, palmitoyl or stearoyl; (methoxy, ethoxy, n- or i-propoxy or n-butoxy)-carbonyl. Said lower alkenyl, alkynyl or hydroxy-alkyl groups are preferably, allyl, methallyl, 2- or 3-butenyl; propargyl, 2- or 3-butynyl; 2-hydroxy-(ethyl or propyl), 3-hydroxy-(propyl or butyl) or 4-hydroxybutyl.

The terms "lower" and "higher" referred to above and hereinafter in connection with organic radicals or compounds, define such with up to 7, preferably up to 4, especially with up to 2 carbon atoms; or such with 8 to 18, preferably 8 to 14 carbon atoms respectively.

The compounds of formula I, with R being alkyl, alkenyl, alkynyl or hydroxyalkyl, form lower alkyl-quaternaries at said piperazine-4-position, and the anions thereof, as well as the salts of all compounds of formula I, are derived from the pharmaceutically acceptable acids listed below.

The compounds of the invention exhibit valuable pharmacological properties. Besides some hypolipidemic effects, they show primarily anticonvulsant activity, as can be demonstrated in classical animal tests, using advantageously mammals, such as mice or rats, as tests objects. Said compounds can be applied to such mammals suffering from hyperlipidemia, agitation and/or convulsions, either enterally or parenterally, e.g. orally, intraperitoneally or intravenously, for example in the form of starchy suspensions or aqueous solutions respectively. The dosage may range between about 1 and about 500 mg/kg/day, preferably between about 2 and 200 mg/kg/day, and especially between about 5 and 10 mg/kg/day. Hypolipidemic effects are measured, for example, by direct lipid-estimation in orbital blood of said mammals, and the anticonvulsant activity is observed by their protection against electrically or chemically induced seizures, such as the mouse or rat minimum or maximum electroshock, or seizures caused by 1,5-pentamethylenetetrazole, picrotoxin or thiosemicarbazide. According to these tests the compunds of the invention, when administered to the mammals either enterally or parenterally, e.g. orally, intraperitoneally or intravenously, and at regular intervals between 0.5 and 24 hours later, preferably at peak effect, they are given an electric shock, e.g. to mice 50 milliamperes of current and 0.2 second duration through corneal electrodes, from which all animals recover. Those animals not exhibiting a tonic hindlimb extensor seizure are considered protected. Rats may also be bled at regular intervals and the blood-lipids estimated according to standard methods. Moreover, rats may receive the compounds orally or intraperitoneally, and 1.5 or 3.5 hours later, for example, 24 mg/kg of 1,5-pentamethylenetetrazole intravenously. They are checked immediately for the presence of clonic seizures of at least 5 seconds duration and all animals not exhibiting them are also considered protected. Furthermore, the effects of said compounds are observed in mice and rats at 0.25-24 hours after various oral or intraperitoneal doses and their performance at the rotorod is estimated, as well as various other effects, e.g. catalepsy, hypothermia, unconditioned escape etc. According to the test results obtained, the compounds of the invention are useful as mild hypolipidemic, and especially good anticonvulsant agents, for example, in the treatment or management of epilepsy (grand mal) or other spastic conditions. They are also useful intermediates in the preparation of other valuable products, preferably of corresponding pharmaceutical compositions.

Particularly useful are compounds of Formula I, wherein each of Ph and Ph' is 1,2-phenylene, unsubstituted or substituted by up to 2 members selected from lower alkyl, hydroxy, lower alkoxy, benzyloxy, lower alkylthio and halogeno, or by one member selected from lower alkylenedioxy, trifluoromethyl, nitro, amino, lower mono- or dialkylamino; each of alk and alk' is ethylene, 1,2- or 1,3-propylene; and R is hydrogen, lower or higher alkyl or alkanoyl, lower alkoxycarbonyl, lower alkenyl, lower alkynyl or lower hydroxyalkyl, wherein the multiple bond or hydroxy group is separated from the nitrogen atom by at least 2 carbon atoms; lower alkyl-quaternaries or pharmaceutically acceptable acid addition salts thereof.

Outstanding on account of their anticonvulsant activity are the compounds of Formula II

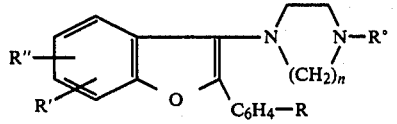

wherein R is hydrogen, lower alkyl or halogeno; each of R' and R" is hydrogen, lower alkyl or lower alkoxy, or both (R'+R") are lower alkylenedioxy; n is the integer 2 or 3; and R° is hydrogen, lower alkyl or lower hydroxyalkyl with hydroxy separated from the nitrogen atom by at least 2 carbon atoms; or pharmaceutically acceptable acid addition salts thereof.

Most preferred are compounds of Formula II, wherein R is hydrogen, methyl or chloro; each of R' and R" is hydrogen, methyl, methoxy or chloro, or (R'+R") are methylenedioxy, preferably in the 5- and 6-positions; n is 2; and R° is methyl or 2-hydroxyethyl; or pharmacuetically acceptable acid addition salts thereof.

The compounds of the invention are prepared by ring-closing the compounds of Formula III

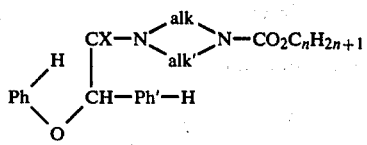

wherein n is an integer from 1 to 7, X defines oxy or thio and the remaining symbols have the meaning given for Formula I and, if desired: (a) hydrolyzing or reducing resulting compounds of Formula I to those which R=H or methyl and/or (Ph, Ph')=$C_6H_4$ or (hydroxy, amino)-1,2-phenylene; (b) condensing or quaternizing said resulting compounds with reactive lower or higher alkanoic acid derivatives or alkyleneoxides; (c) reducing resulting compounds wherein R=alkanoyl to those with R=alkyl, and/or converting resulting compounds into pharmaceutically acceptable acid addition salts thereof.

Said ring-closing is carried out in the presence of acidic condensing agents, such as inorganic acid halides, e.g. phosphorus oxyhalides, advantageously at temperatures between about 50° and 150°, preferably at about 100°.

The resulting lower alkoxycarbonyl derivatives of formula I may either be hydrolyzed to those with R=H, for example, with aqueous bases, such as alkali metal hydroxides or carbonates, or reduced to those with R=methyl, for example, with the use of simple or complex light metal hydrides, such as diborane or alane, alkali metal boro- or aluminumhydrides or -alkoxyhydrides, e.g. lithium aluminumhydride and/or sodium trimethoxyborohydride. Depending on the presence of other reducible groups, e.g. benzyloxy, chloro, nitro within Ph and/or Ph', such compounds I may also or further be reduced with the use of catalytically activated or nascent hydrogen, such as hydrogen in the presence of cobalt, palladium, platinum or rhodium catalysts, e.g., cobalt sulfide or tris-(triphenylphosphine)-rhodium chloride (which latter are not poisoned by sulfur); or hydrogen generated electrolytically; or other reducing agents, such as hydrazine, for elimination of Cl.

Said resulting compounds can be condensed with corresponding reactive esters of the alcohols R—OH, for example, such esterified by a strong inorganic or organic acid, above all a hydrohalic acid, e.g. hydrochloric, hydrobromic or hydriodic acid; sulfuric or an aromatic sulfonic acid, e.g. p-toluene or m-bromobenzene sulfonic acid. Said condensation is preferably carried out in the presence of a basic condensation agent, such as an alkali or alkaline earth metal hydroxide, carbonate or bicarbonate, e.g. sodium, potassium or calcium hydroxide or carbonate; alkali metal hydrides, lower alkoxides or alkanoates, e.g. sodium hydride, methylate or acetate, as well as organic tertiary nitrogen bases, such as tri-lower alkylamines or pyridines, e.g. triethylamine or lutidine. Depending on the stoichiometric amount of said esters, the compounds of formula I chosen, as well as the basicity of said condensation agents, compounds I are obtained wherein R is different from hydrogen and/or Ph, Ph' are (lower alkoxy and/or mono- or di-lower alkylamino)-1,2-phenylene, or said lower alkyl-quaternaries thereof. Said compounds I with R=H may also be acylated with said reactive alkanoic acid derivatives, advantageously halides, anhydrides or esters, e.g. cyanomethyl esters, and the resulting amides reduced as described above for said lower alkoxycarbonyl derivatives; or hydroxyalkyl is introduced by addition of lower alkyleneoxides, e.g. ethyleneoxide.

Finally, the compounds of the invention are either obtained in the free, basic form, or as a salt thereof. Any resulting base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, basic salt or cation exchange, e.g. an alkali metal hydroxide or carbonate. Said acid addition salts are either those of inorganic or organic acids, such as strong metalloidic acids, for example hydrohalic, e.g. hydrochloric or hydrobromic acid; sulfuric, phosphoric, nitric or perchloric acid; or aliphatic or aromatic carboxylic or sulfonic acids, e.g. formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound of formula I and II is referred to in this context, a corresponding salt is also intended, provided such is possible or appropriate under the circumstances.

The starting material of formula III is known or, if new, can be prepared according to the known procedures and those illustrated in the examples herein. Said "α-Phenoxy-β Thiophenoxyphenylacetic Acid Derivatives" corresponding to III are described in the Indian Journal of Chemistry, Vol. 8, pages 1086–1095 (1970), as "Hypoglycaemic Agents".

In case mixtures of position and geometrical or optical isomers of the compounds of formulae I to III are obtained, these can be separated into the single isomers by methods in themselves known, e.g. by fractional distillation, crystallization and/or chromatography. Racemic products can likewise be resolved into the optical antipodes, for example, by separation of diastereomeric salts thereof, e.g., by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g. those of formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweetners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods respectively and contain about 0.1 to 75%, preferably about 1 to 50% of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

The mixture of 4,070 g of 1-[α-(4-methoxyphenoxy)-phenylacetyl]-4-ethoxycarbonyl piperazine, 20,000 ml of toluene and 2,850 ml of phosphorus oxychloride is stirred under nitrogen at 98° for 24 hours. It is poured hot onto 100 kg of crushed ice, followed by 10,000 ml of 50% aqueous sodium hydroxide. After stirring for 30 minutes the organic phase is separated and the aqueous layer extracted with 10,000 ml of toluene. The combined toluene solutions are washed with 10,000 ml of 2 N aqueous sodium hydroxide and 4 times with 10,000 ml of water, dried, filtered and evaporated at about 60°, to yield the 1-(5-methoxy-2-phenyl-3-benzofuryl)-4-ethoxycarbonylpiperazine showing in the NMR-spectrum peaks centered at 8.09, 3.72 and 3.12 ppm.

The starting material is prepared as follows: To the solution of 1,032 g of sodium methoxide in 12,000 ml of methanol 2,361 g of 4-methoxyphenol are added while stirring under nitrogen at 40°. After 30 minutes 4,100 g of methyl α-bromophenylacetate are added during 10 minutes and the mixture is refluxed for 5 hours. It is combined with 14,000 ml of 2 N aqueous sodium hydroxide and refluxing is continued for an additional hour. The mixture is stirred at room temperature overnight, diluted with 14,000 ml of water at 65° and 3,000 ml of concentrated hydrochloric acid are added during 1 hour. Stirring is continued for 2 hours at room temperature, the precipitate formed is filtered off and washed 3 times with 4,000 ml of water, to yield the α-(4-methoxyphenoxy)-phenylacetic acid melting at 108°–110°.

The mixture of 2,938 g thereof, 7,000 ml of toluene and 2,000 ml of thionyl chloride is stirred under nitrogen at 95°–98° for 3.5 hours and evaporated at 60°. The residue is taken up in 4,500 ml of methylene chloride and the solution added to that of 1,800 g of 1-ethoxycarbonylpiperazine in 12,000 ml of methylene chloride while stirring under nitrogen at 0°–5° for one hour. The mixture is stirred at room temperature overnight whereupon 12,000 ml of water are added during 15 minutes. The organic phase is separated, washed with 4,000 ml of N-hydrochloric acid, followed twice by 4,000 ml of water, 4,000 ml of N-aqueous sodium hydroxide and water again. It is dried, filtered and evaporated at 50°, to yield the 1-[α-(4-methoxyphenoxy)-phenylacetyl]-4-ethoxycarbonylpiperazine showing in the IR-spectrum bands at 1691, 1638 and 815 cm$^{-1}$.

EXAMPLE 2

To the suspension of 560 g of lithium aluminumhydride in 32,000 ml of diethyl ether, the solution of 3,717 g of 1-(5-methoxy-2-phenyl-3-benzofuryl)-4-ethoxycarbonylpiperazine in 20,000 ml of diethyl ether is added during 2 hours while stirring under nitrogen at 0°. Stirring is continued for 4 hours at 24° and 1,000 ml of water are slowly added at 0°, followed by 500 ml of 3 N aqueous sodium hydroxide. The resulting suspension is stirred overnight at room temperature, filtered and the residue washed with 8,000 ml of diethyl ether. The filtrate is evaporated and 2,838 g of the residue taken up in 16,000 ml of isopropanol. The solution is acidified with 750 ml of 12 N ethanolic hydrogen chloride while stirring under nitrogen at 40°, and stirring is continued for 3 hours at room temperature. The precipitate formed is filtered off, washed with 4,000 ml of isopropanol, dried and 1,600 g thereof are dissolved in 24,000 ml of water. The solution is made basic with 720 g of 50% aqueous sodium hydroxide and extracted with a total of 40,000 ml of diethyl ether. The extract is dried, filtered, evaporated, the residue distilled and the fraction boiling at 190°–200°/0.1 mm Hg collected. 1.325 g of the distillate are dissolved in 5,300 ml of methanol and the solution acidified at 0° with 627 ml of 7.2 N methanolic hydrogen chloride. After stirring for 3 hours at 0° the precipitate formed is filtered off and washed with 1,000 ml of cold methanol, to yield the 1-(5-methoxy-2-phenyl-3-benzofuryl)-4-methylpiperazine hydrochloride melting at 304°–306°. If desired, 1,207 g thereof may be recrystallized from 19,200 ml of boiling methanol, yielding somewhat larger crystals of identical melting point.

EXAMPLE 3

The mixture of 38.0 g of the previously obtained (Ex. 1) 1-(5-methoxy-2-phenyl-3-benzofuryl)-4-ethoxycarbonylpiperazine, 400 ml of 95% aqueous ethanol and 50 ml of 50% aqueous sodium hydroxide is stirred at reflux for 18 hours and evaporated. The residue is taken up in water, the mixture extracted with diethyl ether, the extract washed with saturated aqueous sodium chloride, dried and evaporated. The residue is dissolved in hot isopropanol, the solution decolorized with charcoal, acidified with ethereal hydrodgen chloride and the precipitate formed filtered off, to yield the 1-(5-methoxy-2-phenyl-3-benzofuryl)-piperazine melting at 283°–285° with decomposition.

EXAMPLE 4

The solution of 7.8 g of 1-(5-methoxy-2-phenyl-3-benzofuryl)piperazine in 25 ml of methanol and 0.5 ml of water is treated with 3.8 ml of an 8.0 molar solution of ethylene oxide in methanol. The mixture is stirred at 48° for 18 hours and evaporated. The residue is dissolved in hot isopropanol, the solution acidified with ethereal hydrogen chloride and the precipitate formed collected, to yield the 1-(5-methoxy-2-phenyl-3-benzofuryl)-4-(2-hydroxyethyl)-piperazine hydrochloride melting at 237°–239° with decomposition.

EXAMPLE 5

To the solution of 56 g of 1-(2-p-chlorophenyl-3-benzofuryl)piperazine in 25.2 g of triethylamine and 500 ml of methylene chloride, 31.7 g of pelargonic acid chloride in 300 ml of methylene chloride are added while stirring at 0° for ½ hour and stirring is continued for 15 hours. The mixture is washed successively with 1 N-hydrochloric acid, 2 N-aqueous sodium hydroxide and saturated aqueous sodium chloride, dried and evaporated to yield the 1-(2-p-chlorophenyl-3-benzofuryl)-4-pelargonylpiperazine as an oil showing in the IR-spectrum characteristic bands at 1640 and 812 cm$^{-1}$.

EXAMPLE 6

To the suspension of 9.3 g of lithium aluminumhydride in 200 ml of diethyl ether (anhydr.) is added dropwise the solution of 73.3 g of 1-(2-p-chlorophenyl-3-benzofuryl)-4-pelargonylpiperazine in the mixture of 500 ml of diethyl ether and 200 ml of tetrahydrofuran while stirring at 0°. After addition, the suspension is stirred at ambient temperature for 15 hours, then cooled again to 0° and successively combined with 9.3 ml of water, 9.3 ml of 15% aqueous sodium hydroxide and 27.9 ml of water. The suspension is stirred in the ice-bath for 1 hour, filtered and the residue washed with diethyl ether. The filtrate is dried, evaporated, the residue taken up in the minimum amount of isopropanol and the solution acidified with ethereal hydrogen chloride, to yield the 1-(2-p-chlorophenyl-3-benzofuryl)-4-n-nonylpiperazine hydrochloride melting at 268°–270° with decomposition.

EXAMPLE 7

The mixture of 13.5 g of 1-(5-benzyloxy-2-phenyl-3-benzofuryl)-4-methylpiperazine hydrochloride, 125 ml of ethanol and 2.5 g of 10% palladium on charcoal is hydrogenated at a pressure of 2.7 atm and at ambient temperature until the hydrogen uptake ceases. The catalyst is filtered off, the filtrate evaporated and the residue triturated with acetone to afford the crystalline 1-(5-hydroxy-2-phenyl-3-benzofuryl)-4-methylpiperazine hydrochloride monohydrate melting at 253°–256° with decomposition.

EXAMPLE 8

The mixture of 6.0 g of 1-(4-methoxy-7-chloro-2-phenyl-3-benzofuryl)-4-methylpiperazine hydrochloride, 45 ml of hydrazine hydrate, 250 ml of ethanol and 1.5 g of 10% palladium on charcoal is stirred at reflux for 2 hours. It is filtered, the filtrate evaporated, the residue taken up in methylene chloride and successively washed with 2 N aqueous sodium hydroxide and saturated aqueous sodium chloride, dried and evaporated. The residue is taken up in isopropanol, the solution acidified with ethereal hydrogen chloride and the precipitate collected to yield the 1-(4-methoxy-2-phenyl-3-benzofuryl)-4-methylpiperazine hydrochloride melting at 279°–282° with decomposition. This elimination of chlorine from said 7-position ensures that the process according to Example 1 provided said 4-methoxy-starting material (identified in Example 9, No. 33) unambiguously.

EXAMPLE 9

The mixture of 8.9 g of 1-(5-methoxy-2-phenyl-3-benzofuryl)piperazine, 3.8 g of allyl bromide, 4.0 g of anhydrous potassium carbonate and 150 ml of acetone is stirred at reflux for 10 hours. It is filtered, the filtrate evaporated, the residue taken up in diethyl ether and the solution washed with water and saturated aqueous sodium chloride. It is evaporated, the residue dissolved in isopropanol and the solution acidified with ethereal hydrogen chloride, to yield the 1-(5-methoxy-2-phenyl-3-benzofuryl)-4-allylpiperazine hydrochloride melting at 265°–268° with decomposition.

The mixture of 8.2 g of 1-(5-methoxy-2-phenyl-3-benzofuryl)piperazine, 15 g of methyl iodide and 25 ml of anhydrous ethanol is stirred at room temperature for one hour. It is filtered and the residue recrystallized from ethanol, to yield the 1-(5-methoxy-2-phenyl-3-benzofuryl)-4,4-dimethylpiperazinium iodide; m.p. 253°–255° d.

EXAMPLE 10

Analogous to the methods illustrated by the previous examples, the following compounds of formula I are prepared from equivalent amounts of the corresponding starting materials. Substituents in "Ph", i.e. the benzofuryl-positions, are identified as 4-A, 5-B, 6-C and 7-D; alk'=(CH$_2$)$_2$; oils are identified by NMR-peaks in ppm and all melting points (m.p.) are given in °C. and occur with decomposition; h=hemihydrate:

which are granulated, if necessary, with an additional amount of water. The granulate is dried overnight at 35°, broken on a screen with 1.2 mm openings and compressed into tablets using concave punches with 10.3

| No. | A | B | C | D | H—Ph' | alk | R | Salt | NMR or m.p. |
|---|---|---|---|---|---|---|---|---|---|
| 1 | H | H | H | H | C$_6$H$_5$ | (CH$_2$)$_2$ | CO$_2$C$_2$H$_5$ | — | 8.18, 3.68, 3.17 |
| 2 | H | H | H | H | p-Cl—C$_6$H$_4$ | (CH$_2$)$_2$ | CO$_2$C$_2$H$_5$ | — | 8.08, 3.59, 3.15 |
| 3 | H | CH$_3$ | CH$_3$ | H | C$_6$H$_5$ | (CH$_2$)$_2$ | CO$_2$C$_2$H$_5$ | — | 8.13, 3.63, 2.27 |
| 4 | H | C(CH$_3$)$_3$ | H | H | C$_6$H$_5$ | (CH$_2$)$_2$ | CO$_2$C$_2$H$_5$ | — | 8.12, 3.62, 1.37 |
| 5 | H | OCH$_3$ | H | H | C$_6$H$_5$ | (CH$_2$)$_3$ | CO$_2$C$_2$H$_5$ | — | 8.12, 3.68, 3.37 |
| 6 | H | OCH$_3$ | H | H | p-Cl—C$_6$H$_4$ | (CH$_2$)$_2$ | CO$_2$C$_2$H$_5$ | — | 8.05, 3.74, 3.61 |
| 7 | H | H | OCH$_3$ | H | C$_6$H$_5$ | (CH$_2$)$_2$ | CO$_2$C$_2$H$_5$ | — | 8.15, 3.75, 3.65 |
| 8 | H | H | H | OCH$_3$ | C$_6$H$_5$ | (CH$_2$)$_2$ | CO$_2$C$_2$H$_5$ | — | 8.12, 3.87, 3.57 |
| 9 | OCH$_3$ | H | H | Cl | C$_6$H$_5$ | (CH$_2$)$_2$ | CO$_2$C$_2$H$_5$ | — | 8.16, 3.79, 3.59 |
| 10 | H | benzyl-O | H | H | C$_6$H$_5$ | (CH$_2$)$_2$ | CO$_2$C$_2$H$_5$ | — | 8.09, 5.02, 3.62 |
| 11 | H | O—CH$_2$—O | | H | C$_6$H$_5$ | (CH$_2$)$_2$ | CO$_2$C$_2$H$_5$ | — | 8.05, 5.87, 3.60 |
| 12 | H | Cl | H | H | C$_6$H$_5$ | (CH$_2$)$_2$ | CO$_2$C$_2$H$_5$ | — | 8.07, 3.55, 3.08 |
| 13 | H | H | Cl | H | C$_6$H$_5$ | (CH$_2$)$_2$ | CO$_2$C$_2$H$_5$ | — | 8.07, 3.61, 3.17 |
| 14 | H | Cl | H | H | p-Cl—C$_6$H$_4$ | (CH$_2$)$_2$ | CO$_2$C$_2$H$_5$ | — | 8.12, 3.62, 3.14 |
| 15 | H | H | Cl | H | p-Cl—C$_6$H$_4$ | (CH$_2$)$_2$ | CO$_2$C$_2$H$_5$ | — | 8.02, 3.59, 3.14 |
| 16 | H | H | H | H | p-Cl—C$_6$H$_4$ | (CH$_2$)$_2$ | H | HCl | 247–249° |
| 17 | H | H | H | H | C$_6$H$_5$ | (CH$_2$)$_2$ | H | HCl | 237–239° |
| 18 | H | CH$_3$ | CH$_3$ | H | C$_6$H$_5$ | (CH$_2$)$_2$ | H | HCl | 260–264° |
| 19 | H | OCH$_3$ | H | H | p-Cl—C$_6$H$_4$ | (CH$_2$)$_2$ | H | HCl | 296–298° |
| 20 | H | H | OCH$_3$ | H | C$_6$H$_5$ | (CH$_2$)$_2$ | H | HCl | 249–252° |
| 21 | H | H | H | OCH$_3$ | C$_6$H$_5$ | (CH$_2$)$_2$ | H | HCl | 249–251° |
| 22 | H | benzyl-O | H | H | C$_6$H$_5$ | (CH$_2$)$_2$ | H | HCl h | 290–293° |
| 23 | H | O—CH$_2$—O | | H | C$_6$H$_5$ | (CH$_2$)$_2$ | H | HCl | 326–328° |
| 24 | H | Cl | H | H | C$_6$H$_5$ | (CH$_2$)$_2$ | H | HCl | 266–268° |
| 25 | H | H | H | H | C$_6$H$_5$ | (CH$_2$)$_2$ | CH$_3$ | HCl | 264–266° |
| 26 | H | H | H | H | p-Cl—C$_6$H$_4$ | (CH$_2$)$_2$ | CH$_3$ | HCl | 300–303° |
| 27 | H | CH$_3$ | CH$_3$ | H | C$_6$H$_5$ | (CH$_2$)$_2$ | CH$_3$ | HCl | 296–299° |
| 28 | H | C(CH$_3$)$_3$ | H | H | C$_6$H$_5$ | (CH$_2$)$_2$ | CH$_3$ | HCl | 297–299° |
| 29 | H | OCH$_3$ | H | H | C$_6$H$_5$ | (CH$_2$)$_2$ | CH$_3$ | CH$_3$SO$_3$H | 207–209° |
| 30 | H | OCH$_3$ | H | H | p-Cl—C$_6$H$_4$ | (CH$_2$)$_2$ | CH$_3$ | HCl | 290–293° |
| 31 | H | H | OCH$_3$ | H | C$_6$H$_5$ | (CH$_2$)$_2$ | CH$_3$ | HCl | 256–258° |
| 32 | H | H | H | OCH$_3$ | C$_6$H$_5$ | (CH$_2$)$_2$ | CH$_3$ | HCl h | 267–269° |
| 33 | OCH$_3$ | H | H | Cl | C$_6$H$_5$ | (CH$_2$)$_2$ | CH$_3$ | HCl | 282–284° |
| 34 | H | benzyl-O | H | H | C$_6$H$_5$ | (CH$_2$)$_2$ | CH$_3$ | HCl h | 221–224° |
| 35 | H | O—CH$_2$—O | | H | C$_6$H$_5$ | (CH$_2$)$_2$ | CH$_3$ | HCl | 285–288° |
| 36 | H | Cl | H | H | C$_6$H$_5$ | (CH$_2$)$_2$ | CH$_3$ | HCl | 310–311° |
| 37 | H | H | Cl | H | C$_6$H$_5$ | (CH$_2$)$_2$ | CH$_3$ | HCl | 270–272° |
| 38 | H | Cl | H | H | p-Cl—C$_6$H$_4$ | (CH$_2$)$_2$ | CH$_3$ | HCl | 320–323° |
| 39 | H | H | Cl | H | p-Cl—C$_6$H$_4$ | (CH$_2$)$_2$ | CH$_3$ | HCl | 296–299° |
| 40 | H | OCH$_3$ | H | H | C$_6$H$_5$ | (CH$_2$)$_3$ | CH$_3$ | — | 68–70° |
| 41 | H | H | H | OCH$_3$ | C$_6$H$_5$ | (CH$_2$)$_2$ | C$_2$H$_4$OH | HCl | 227–229° |
| 42 | H | O—CH$_2$—O | | H | C$_6$H$_5$ | (CH$_2$)$_2$ | C$_2$H$_4$OH | HCl | 249–252° |
| 43 | H | Cl | H | H | C$_6$H$_5$ | (CH$_2$)$_2$ | C$_2$H$_4$OH | HCl | 251–254° |
| 44 | H | OCH$_3$ | H | H | C$_6$H$_5$ | (CH$_2$)$_2$ | propargyl | HCl | 235–237° |
| 45 | CH$_3$ | CH$_3$ | H | H | C$_6$H$_5$ | (CH$_2$)$_2$ | CH$_3$ | HCl | 281–283° |
| 46 | OCH$_3$ | OCH$_3$ | H | H | C$_6$H$_5$ | (CH$_2$)$_2$ | CH$_3$ | HCl | 294–295° |
| 47 | H | SCH$_3$ | H | H | C$_6$H$_5$ | (CH$_2$)$_2$ | CH$_3$ | HCl | 301–304° |

EXAMPLE 11

Preparation of 10,000 tablets each containing 100.0 mg of the active ingredient:
Formula:

| | |
|---|---|
| 1-(5-methoxy-2-phenyl-3-benzofuryl)-4-methylpiperazine hydrochloride | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

Preparation of 10,000 capsules each containing 50.0 mg of the active ingredient:
Formula:

| | |
|---|---|
| 1-(5-methoxy-2-phenyl-3-benzofuryl)-4-methylpiperazine hydrochloride | 500.0 g |
| Lactose | 2,350.0 g |
| Talcum powder | 150.0 g |

Procedure:

All the powders are passed through a screen with openings of 0.6 mm. Then the drug substance is placed in a suitable mixer and mixed first with the talcum, then with the lactose until homogenous. No. 2 capsules are filled with 300 mg of the mixture, using a capsule filling machine.

Analogously, tablets and capsules are prepared from the other compounds illustrated in the previous examples.

I claim:

1. A 1-(2-phenyl-3-benzofuryl)-piperazine compound of the formula

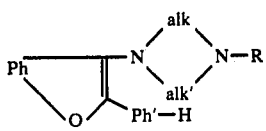

wherein each of Ph and Ph' is 1,2-phenylene, unsubstituted or substituted by up to 3 members selected from the group consisting of lower alkyl, hydroxy, lower alkoxy, benzyloxy, lower alkylenedioxy, lower alkylthio, halogeno, trifluoromethyl, nitro, amino, lower alkylamino and di-lower alkylamino; each of the radicals alk and alk' is lower alkylene separating both nitrogens by 2 or 3 carbon atoms and forming with them a 6 or 7 membered ring; and R is hydrogen, lower or higher alkyl or alkanoyl, lower alkoxycarbonyl, lower alkenyl, lower alkynyl or lower hydroxyalkyl, wherein the multiple bond or hydroxy group is separated from the nitrogen atom by at least 2 carbon atoms; lower alkylquaternaries or pharmaceutically acceptable acid addition salts thereof.

2. A compound as claimed in claim 1, in which formula each of Ph and Ph' is 1,2-phenylene, unsubstituted or substituted by up to 2 members selected from lower alkyl, hydroxy, lower alkoxy, benzyloxy, lower alkylthio and halogeno, or by one member selected from lower alkylenedioxy, trifluoromethyl, nitro, amino, lower mono- or dialkylamino; each of alk and alk' is ethylene, 1,2- or 1,3-propylene; and R is hydrogen, lower or higher alkyl or alkanoyl, lower alkoxycarbonyl, lower alkenyl, lower alkynyl or lower hydroxyalkyl, wherein the multiple bond or hydroxy group is separated from the nitrogen atom by at least 2 carbon atoms; lower alkyl-quaternaries or pharmaceutically acceptable acid addition salts thereof.

3. A compound as claimed in claim 1 and corresponding to the formula

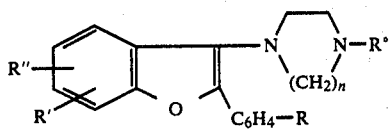

wherein R is hydrogen, lower alkyl or halogeno; each of R' and R" is hydrogen, lower alkyl or lower alkoxy, or both (R'+R") are lower alkylenedioxy; n is the integer 2 or 3; and R° is hydrogen, lower alkyl or lower hydroxylalkyl with hydroxy separated from the nitrogen atom by at least 2 carbon atoms; or pharmaceutically acceptable acid addition salts thereof.

4. A compound as claimed in claim 3, in which formula R is hydrogen, methyl or chloro; each of R' and R" is hydrogen, methyl, methoxy or chloro, or (R'+R") are methylenedioxy; n is 2; and R° is methyl or 2-hydroxyethyl; or pharmaceutically acceptable acid addition salts thereof.

5. A compound as claimed in claim 4, in which formula said substituents R' and R" are in the 5- and 6-positions.

6. A compound as claimed in claim 3 and being the 1-(5-methoxy-2-phenyl-3-benzofuryl)-4-methylpiperazine or a pharmaceutically acceptable acid addition salt thereof.

7. An anticonvulsant pharmaceutical composition comprising a spasmolytically effective amount of a compound claimed in claim 1, together with a pharmaceutical excipient.

8. A method of treating convulsions and other spastic conditions, which comprises administering to mammal suffering from them, enterally or parenterally a spasmolytically effective amount of a composition claimed in claim 7.

* * * * *